United States Patent
Jeon et al.

(10) Patent No.: US 9,945,739 B2
(45) Date of Patent: Apr. 17, 2018

(54) FLEXIBLE PRESSURE SENSOR USING AMORPHOUS METAL AND FLEXIBLE BIMODAL SENSOR FOR SIMULTANEOUSLY SENSING PRESSURE AND TEMPERATURE

(71) Applicant: KOREA UNIVERSITY RESEARCH AND BUSINESS FOUNDATION, Seoul (KR)

(72) Inventors: Sang Hun Jeon, Seoul (KR); Kung Won Rhie, Seoul (KR); Dong Seuk Kim, Sejong-si (KR); Bum Jin Kim, Gunpo-si (KR); Tae Ho Kim, Busan (KR); Min Hyun Jung, Busan (KR)

(73) Assignee: KOREA UNIVERSITY RESEARCH AND BUSINESS FOUNDATION, Seoul (KR)

( * ) Notice: Subject to any disclaimer, the term of this patent is extended or adjusted under 35 U.S.C. 154(b) by 0 days.

(21) Appl. No.: 15/166,824

(22) Filed: May 27, 2016

(65) Prior Publication Data
US 2016/0349134 A1    Dec. 1, 2016

(51) Int. Cl.
*G01L 1/00*    (2006.01)
*G01L 1/14*    (2006.01)
(Continued)

(52) U.S. Cl.
CPC .............. *G01L 1/14* (2013.01); *A61B 34/00* (2016.02); *G01L 1/18* (2013.01); *G06F 2203/04105* (2013.01); *Y10S 901/46* (2013.01)

(58) Field of Classification Search
CPC ..... G01L 9/0052; G01L 19/0092; G01L 1/20; Y10S 901/46; G01N 27/227
(Continued)

(56) References Cited

U.S. PATENT DOCUMENTS 4,771,639 A * 9/1988 Saigusa ................. G01L 9/0055
29/621.1
7,017,419 B2 * 3/2006 Pedersen ............... G01L 9/0073
73/718
(Continued)

FOREIGN PATENT DOCUMENTS

| JP | 20130004076 | 1/2013 |
| KR | 101177543 | 1/2006 |
| KR | 1020150028125 | 3/2015 |

OTHER PUBLICATIONS

Choong, Chwee-Lin; et al., "Highly Stretchable Resistive Pressure Sensors Using a Conductive Elastomeric Composite on a Micropyramid Array," Samsung Advanced Institute of Technology, Yongin-si Gyeonggi-do , Korea, 2014 Wiley-VCH Verlag GmbH & Co. KGaA, Weinheim.

*Primary Examiner* — Max Noori
(74) *Attorney, Agent, or Firm* — Hauptman Ham, LLP

(57) ABSTRACT

Provided are a flexible pressure sensor using an amorphous metal and a flexible bimodal sensor for simultaneously sensing a pressure and a temperature. The sensors according to an exemplary embodiment of the present invention include a conductive layer formed of the amorphous metal to have stretchable characteristics so that it may be used for an electronic skin. Therefore, these sensors may firmly maintain conductivity and sense a pressure or simultaneously sense a pressure and a temperature even in a state in which various kinds of physical external force are present. In addition, the flexible bimodal sensor according to an exemplary embodiment of the present invention is a novel element for an electronic skin that may simultaneously sense a pressure and a temperature using the amorphous metal.

9 Claims, 6 Drawing Sheets

(51) Int. Cl.
  *G01L 1/18*       (2006.01)
  *A61B 34/00*      (2016.01)

(58) Field of Classification Search
  USPC .............................. 73/780, 862.626, 862.68
  See application file for complete search history.

(56)             References Cited

U.S. PATENT DOCUMENTS

| | | | |
|---|---|---|---|
| 2005/0196877 A1* | 9/2005 | Weinberg ......... | G01N 33/54373 436/518 |
| 2006/0137487 A1* | 6/2006 | McKinnon ............ | B22F 1/0018 75/252 |
| 2013/0048339 A1* | 2/2013 | Tour ........................ | H01B 1/04 174/126.1 |
| 2014/0087952 A1* | 3/2014 | Nam ........................ | G01J 1/42 505/181 |
| 2014/0350348 A1* | 11/2014 | Tee ...................... | A61B 5/0002 600/300 |
| 2015/0059486 A1* | 3/2015 | Choong ................ | G01L 1/2206 73/727 |
| 2016/0329121 A1* | 11/2016 | Xiao ........................ | H01B 1/02 |

* cited by examiner

FIG. 2

| Bending Resistance | Aperture | 1.6 mm | 1.0 mm | 1.7/mm | 0.6 mm | Folding |
|---|---|---|---|---|---|---|
| Pt/FeZr/PET | 3.238468Ω/□ | 3.279175Ω/□ | 3.369635Ω/□ | 25.143357Ω/□ | 103.53117Ω/□ | 280.389810Ω/□ |
| Pt/Ta/PET | 2.768076Ω/□ | 2.808783Ω/□ | 3.763136Ω/□ | 41.145731Ω/□ | 320.89310Ω/□ | 621.645640Ω/□ |
| Pt/Ti/PET | 5.56329Ω/□ | 7.1870470Ω/□ | 7.544364Ω/□ | 61.494708Ω/□ | 645.911580Ω/□ | 3829.35270Ω/□ |

FLEXIBLE PRESSURE SENSOR USING AMORPHOUS METAL AND FLEXIBLE BIMODAL SENSOR FOR SIMULTANEOUSLY SENSING PRESSURE AND TEMPERATURE

CROSS-REFERENCE TO RELATED APPLICATIONS

This application claims priority under 35 U.S.C. § 119 to Korean Patent Application No. 10-2015-0076228, filed on May 29, 2015, in the Korean Intellectual Property Office, the disclosure of which is incorporated herein by reference in its entirety.

TECHNICAL FIELD

The following disclosure relates to a flexible pressure sensor using an amorphous metal and a flexible bimodal sensor for simultaneously sensing a pressure and a temperature. More particularly, the following disclosure relates to flexible sensors corresponding to sensors for an electronic skin and capable of firmly maintaining conductivity and sensing a pressure or simultaneously sensing a pressure and a temperature even in a state in which various kinds of physical external force are present.

BACKGROUND

An electronic skin for a robot is an element designed in order to ultimately provide a skin similar to a skin of a human to the robot. A touch sensor forming the electronic skin is used for a user interface through which a machine and a human being may communicate with each other. The electronic skin configured of a network of electronic elements sensing a touch may be utilized for a high performance wearable electronic device attached onto the skin.

A touch sensor having flexibility as well as a function of sensing temperature and pressure gradients is the next-generation technology, and may also be applied to a user interface of a mobile device and the next-generation wearable computer. In addition, the electronic skin may be utilized for a biomimetic prosthetic device used in an intelligent robot and a rehabilitation medicine. Further, the electronic skin may be used for an interface of a remote medical robot, or the like.

In the case of configuring a conductive layer of a pressure sensor, which is a kind of touch sensor, using a conductive nano-tube in the related art, the conductive nano-tube does not have elasticity, such that a phenomenon that the conductive layer cracks or cleaves by external force occurs.

In order to implement a stretchable touch sensor that may be used as the next-generation technology, a flexible conductive layer should be formed in the touch sensor.

SUMMARY

An embodiment of the present invention is directed to providing a novel flexible pressure sensor including a conductive layer formed of an amorphous metal on a flexible substrate.

An embodiment of the present invention is also directed to providing a flexible bimodal sensor for simultaneously sensing a pressure and a temperature by including a conductive layer formed of an amorphous metal on a flexible substrate and further including a component for sensing a temperature.

In one general aspect, a flexible pressure sensor includes: a flexible substrate having a plurality of micro-sized structure bodies formed of a flexible material on one surface thereof; a conductive layer deposited on one surface of the flexible substrate on which the plurality of micro-sized structure bodies are formed and formed of an amorphous metal; and a counter electrode positioned on the conductive layer, wherein the flexible pressure sensor is configured to measure a resistance value generated by a change in a contact area between the counter electrode and the conductive layer depending on a pressure transferred from the outside through the conductive layer and the counter electrode to sense information on the transferred pressure.

The counter electrode may be entirely formed of the amorphous metal, or may have a structure in which a flexible insulating substrate and a metal layer formed of an amorphous metal on one surface of the flexible insulating substrate are stacked, and the metal layer is positioned on the conductive layer so as to face the conductive layer.

The plurality of micro-sized structure bodies may have any one of a pyramidal shape, a cylindrical shape, a conical shape, and a poly-prismatic shape.

In another general aspect, a flexible pressure sensor includes: a flexible substrate having a plurality of micro-sized structure bodies formed of a flexible material on one surface thereof; a conductive layer deposited on an opposite surface to one surface of the flexible substrate on which the plurality of micro-sized structure bodies are formed and formed of an amorphous metal; and a counter electrode positioned on the plurality of micro-sized structure bodies on the flexible substrate and formed of an amorphous metal, wherein the flexible pressure sensor is configured to measure a capacitance value between the conductive layer and the counter electrode changed by a change in a distance between the conductive layer and the counter electrode depending on a pressure transferred from the outside to sense information on the transferred pressure.

In still another general aspect, a flexible bimodal sensor includes: a flexible substrate having a plurality of micro-sized structure bodies formed of a flexible material on one surface thereof; a conductive layer deposited on one surface of the flexible substrate on which the plurality of micro-sized structure bodies are formed and formed of an amorphous metal; a counter electrode positioned on the conductive layer and formed of an amorphous metal; a flexible insulating substrate positioned on an upper surface of the counter electrode; and a conducting wire repeatedly arranged in a zigzag pattern at a predetermined interval on an upper surface of the flexible insulating substrate and formed of an amorphous metal, wherein the flexible bimodal sensor measures a resistance value between the counter electrode and the conductive layer changed by a change in a contact area between the counter electrode and the conductive layer depending on a pressure transferred from the outside to sense information on the transferred pressure, and measures a resistance value of the conducting wire changed depending on a temperature transferred from the outside to sense information on the transferred temperature.

The amorphous metal may be any one of FeZr, CoNi, La—Al_Cu, Al—Sc, ZrTiCuNiBe, AuSi, CuZr, CuPd, CuCo, CuPdCoP, PdAgSi, PdAgSiP, PdAgSiGe, PtCuAg-PBSi, CuZrTi, CuZrTiNi, and CuZrTiAlBe.

A passivation layer formed of any one of a low resistance metal, a crystalline metal, and an oxidation resistant metal may be additionally deposited on a surface of the amorphous metal in order to increase conductivity of the amorphous metal and prevent oxidation of the amorphous metal.

BRIEF DESCRIPTION OF THE DRAWINGS

FIG. 2 is a table representing surface resistance values measured depending on a bending change with respect to an amorphous metal and a crystalline metal.

DETAILED DESCRIPTION OF EMBODIMENTS

Figure 1:
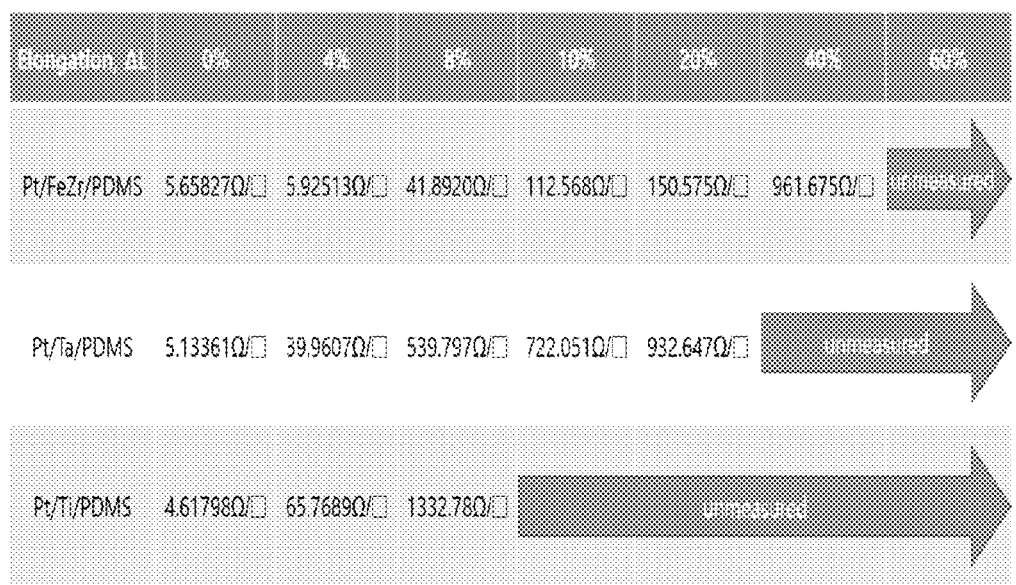
FIG. 1 is a table representing surface resistance values measured depending on a change amount of elongation with respect to an amorphous metal and a crystalline metal.

Hereinafter, exemplary embodiments of the present invention will be described in more detail with reference to the accompanying drawings. It is to be noted that throughout the accompanying drawings, the same components are denoted by the same reference numerals. In addition, a detailed description for the well-known functions and configurations that may unnecessarily make the gist of the present invention unclear will be omitted.

In order to implement an electronic skin imitating a function of a human body, a conductive layer constituting an electronic skin element should have flexibility, and deterioration of conductivity of the conductive layer should be small even with a physical stimulus such as bending, elongation, pressing, or the like.

The present invention is to provide a flexible pressure sensor capable of maintaining flexibility and conductivity even in a state in which an external physical stimulus is present by forming a conductive layer using an amorphous metal, and a flexible bimodal sensor capable of simultaneously measuring a pressure and a temperature.

Characteristics of an amorphous metal for an external physical stimulus will be described with reference to FIGS. 1 and 2.

Since the amorphous metal has an arrangement of atoms dispersed like a liquid, the amorphous metal has a flexible property unlike a crystalline metal.

Referring to FIG. 1, surface resistance values (Ω/square) depending on a change amount (ΔL) of elongation were measured with respect to an element (Pt/FeZr/PDMS) in which an amorphous metal (FeZr) is deposited on a flexible substrate (PDMS) and platinum (Pt) is applied as a passivation layer preventing metal oxidation as well as increasing conductivity onto the amorphous metal.

In addition, surface resistance values (SZ/square) depending on a change amount (ΔL) of elongation were measured with respect to an element (Pt/Ta/PDMS or Pt/Ti/PDMS) in which a crystalline metal (Ta or Ti) is deposited on a flexible substrate (PDMS) and platinum (Pt) is applied as a passivation layer preventing metal oxidation onto the crystalline metal, which is a comparison target element.

As a result, in the element (Pt/FeZr/PDMS) in which the amorphous metal is deposited, a predetermined level of conductivity is maintained even though a length of the element is elongated up to 40% by external force, but in the element (Pt/Ta/PDMS or Pt/Ti/PDMS) in which the crystalline metal is deposited, conductivity is not maintained due to a crack and breakage when a length of the element is elongated to 20% or more or 8% or more by external force. Therefore, it may be appreciated that it is much more excellent to form a conductive layer of a stretchable element using the amorphous metal than to form a conductive layer of a stretchable element using the crystalline metal.

In addition, referring to FIG. 2, surface resistance values (Ω/square) depending on a magnitude change in bending were measured with respect to an element (Pt/FeZr/PET) in which an amorphous metal (FeZr) is deposited on a flexible substrate (PET) and platinum (Pt) is applied as a passivation layer preventing metal oxidation as well as increasing conductivity onto the amorphous metal.

In addition, surface resistance values (Ω/square) depending on a magnitude change in bending were measured with respect to an element (Pt/Ta/PET or Pt/Ti/PET) in which a crystalline metal (Ta or Ti) is deposited on a flexible substrate (PET) and platinum (Pt) is applied as a passivation layer preventing metal oxidation onto the crystalline metal, which is a comparison target element.

In FIG. 2, it may be appreciated that surface resistance values of the element (Pt/FeZr/PET) in which the amorphous metal is deposited are much lower than those of the element (Pt/Ta/PET or Pt/Ti/PET) in which the crystalline metal is deposited even in a state in which the element is completely folded.

As described above, as illustrated in FIGS. 1 and 2, the measured surface resistance values of the element in which the amorphous metal is deposited are much lower than those of the element in which the crystalline metal is deposited, and maintenance of conductivity in a situation in which the external force is present in the element in which the amorphous metal is deposited is more excellent than that in the element in which the crystalline metal is deposited. Therefore, a sensor implemented using the amorphous metal may have flexible characteristics, and may have a small measured resistance value, such that it may be operated even at a very low operation voltage.

Therefore, in the present invention, the amorphous metal will be used to implement a stretchable element for an electronic skin.

Figure 3:
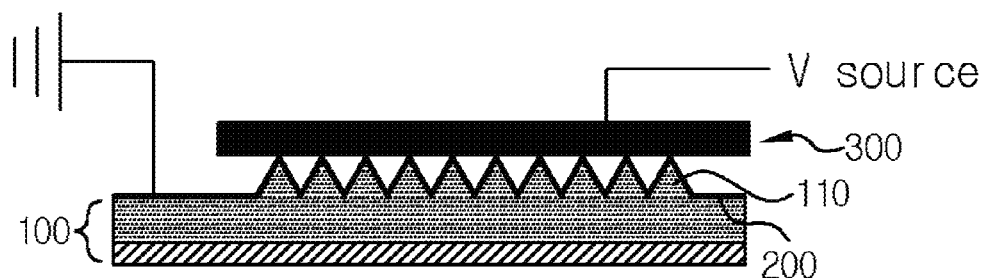
FIG. 3 is a view illustrating a structure of a piezo-resistive flexible pressure sensor according to a first exemplary embodiment of the present invention.
Figure 4:
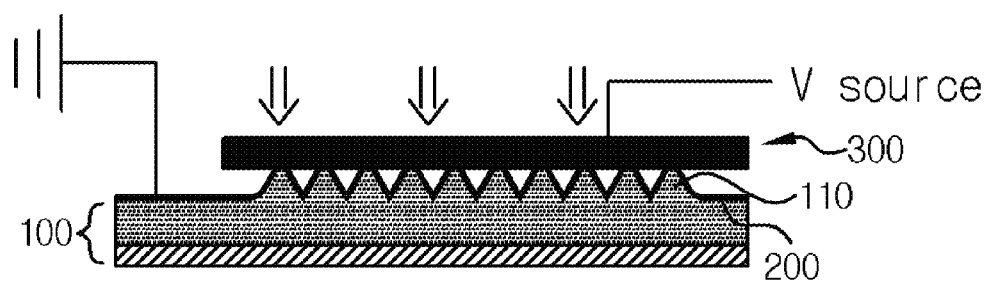
FIG. 4 is a view illustrating a form in the case in which an external pressure is applied to a counter electrode in FIG. 3.
Figure 5:
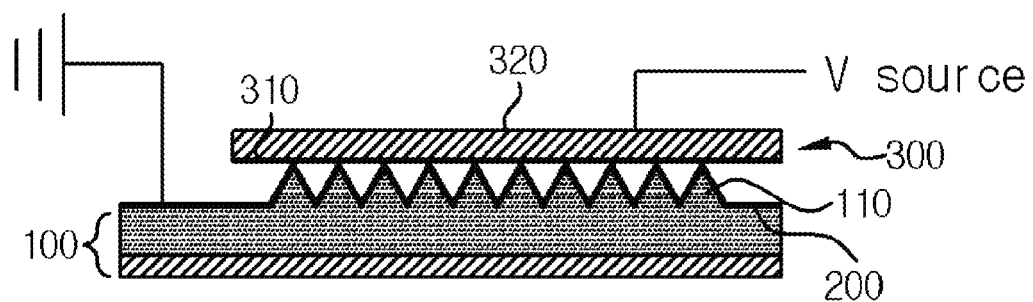
FIG. 5 is a view illustrating a structure of a piezo-resistive flexible pressure sensor according to a second exemplary embodiment of the present invention.

FIGS. 3 to 5 illustrate piezo-resistive flexible pressure sensors according to exemplary embodiments of the present invention. Here, FIG. 4 illustrates a form in the case in which an external pressure is applied to a counter electrode in FIG. 3.

Referring to FIG. 3, a flexible pressure sensor according to an exemplary embodiment of the present invention includes a flexible substrate 100, a conductive layer 200, and a counter electrode 300.

The flexible substrate 100 may have a structure in which a plurality of micro-sized structure bodies 110 are formed of a flexible material, for example, a silicon based rubber such as polydimethylsiloxane (PDMS), polyurethane, or the like, on one surface of a flexible polyethylene phthalate (PET)

substrate, a polycarbonate (PC) substrate, a polyimide (PI) substrate, or a glass substrate having a thickness of several hundreds of micrometers.

Here, as an example, the plurality of micro-sized structure bodies 110 having a pyramidal shape are formed on one surface of the flexible substrate.

The flexible substrate 100 having the micro-sized structure bodies 110 having the pyramid shape may be formed using a silicon mold that may mold the flexible substrate 100. In addition, the plurality of micro-sized structure bodies 110 may have any one of a cylindrical shape, a conical shape, and a poly-prismatic shape, in addition to the pyramidal shape.

The conductive layer 200 is formed of an amorphous metal, and is deposited on one surface of the flexible substrate on which the plurality of micro-sized structure bodies 110 are formed. Therefore, the conductive layer 200 is deposited on the plurality of micro-sized structure bodies 110. The amorphous metal forming the conductive layer 200 may be any one of FeZr, CoNi, La—Al_Cu, Al—Sc, ZrTiCuNiBe, AuSi, CuZr, CuPd, CuCo, CuPdCoP, PdAgSi, PdAgSiP, PdAgSiGe, PtCuAgPBSi, CuZrTi, CuZrTiNi, and CuZrTiAlBe.

In addition, a metal such as gold (Au) or platinum (Pt) may be additionally deposited as a passivation layer on the conductive layer 200 in order to increase conductivity of the conductive layer 200 and prevent oxidation of the conductive layer 200. In addition to the gold or the platinum, a passivation layer (not illustrated) formed of any one of a low resistance metal, a crystalline metal, and an oxidation resistant metal that may increase conductivity of the conductive layer 200 and prevent oxidation of the conductive layer 200 may be additionally deposited on the conductive layer 200.

The counter electrode 300 is positioned on the conductive layer 200 and receives a pressure transferred from the outside. It is preferable that the counter electrode 300 is also formed of an amorphous metal, similar to the conductive layer 200. Therefore, a metal such as gold (Au) or platinum (Pt) may be additionally deposited as a passivation layer on a surface of the counter electrode 300 in order to increase conductivity of the counter electrode 300 and prevent oxidation of the counter electrode 300. In addition to the gold or the platinum, a passivation layer (not illustrated) formed of any one of a low resistance metal, a crystalline metal, and an oxidation resistant metal that may increase conductivity of the counter electrode 300 and prevent oxidation of the counter electrode 300 may be additionally deposited on the surface of the counter electrode 300.

Further, the micro-sized structure bodies 110 having the pyramidal shape are pressed depending on a transferred pressure, such that a contact area between the counter electrode 300 and the conductive layer 200 is changed.

As illustrated in FIG. 3, in the case in which an external pressure is not applied, a contact area between the conductive layer 200 and the counter electrode 300 is small, such that a resistance value measured between the conductive layer 200 and the counter electrode 300 is high. However, as illustrated in FIG. 4, when the external pressure is applied, the micro-sized structure bodies 110 having the pyramidal shape are pressed, such that a contact area between the conductive layer 200 and the counter electrode 300 is increased, whereby a resistance value measured between the conductive layer 200 and the counter electrode 300 is changed to be low.

Therefore, the pressure sensor according to an exemplary embodiment of the present invention applies an operation voltage Vsource to the counter electrode 300 and the conductive layer 200 and measures a resistance value between the counter electrode 300 and the conductive layer 200 to sense information on a pressure applied to the counter electrode 300 depending on a change amount of the resistance value.

A piezo-resistive flexible pressure sensor according to another exemplary embodiment of the present invention illustrated in FIG. 5 is different in a structure of a counter electrode 300 from the piezo-resistive flexible pressure sensor according to an exemplary embodiment of the present invention illustrated in FIGS. 3 and 4.

The counter electrode 300 is not entirely formed of the amorphous metal, as illustrated in FIGS. 3 and 4, but may include a flexible insulating substrate 320 and a metal layer 310 formed on the flexible insulating substrate 320, as illustrated in FIG. 5.

In detail, the counter electrode 300 has a structure in which the insulating substrate 320 such as a flexible PET substrate and the metal layer 310 formed of an amorphous metal on one surface of the insulating substrate 320 are stacked, and the metal layer 310 may be positioned on the conductive layer 200 so as to face the conductive layer 200.

Therefore, a surface of the counter electrode 300 to which an external pressure is applied is formed of the flexible insulating substrate 320, such that even though a person touches the surface, an error in sensing a pressure due to a current in a human body may not occur.

The pressure sensor illustrated in FIG. 5 is configured to apply an operation voltage to the metal layer 310 of the counter electrode 300 and the conductive layer 200 and measures a resistance value between the metal layer 310 of the counter electrode 300 and the conductive layer 200 to sense information on a pressure applied to the counter electrode 300 depending on a change amount of the resistance value. Here, any one of a low resistance metal, a crystalline metal, and an oxidation resistant metal may be additionally deposited as a passivation layer that may increase conductivity of the metal layer 310 and prevent oxidation of the metal layer 310 on a surface of the metal layer 310. Typically, a metal such as gold (Au) or platinum (Pt) may be additionally deposited.

Figure 6:
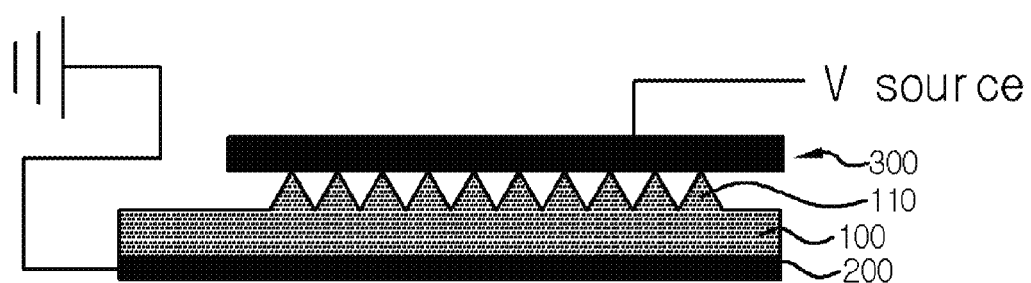
FIG. 6 is a view illustrating a structure of a capacitive flexible pressure sensor according to a first exemplary embodiment of the present invention.
Figure 7:
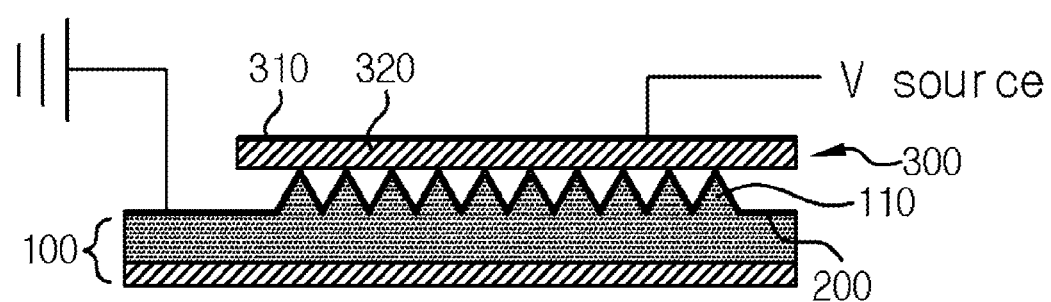
FIG. 7 is a view illustrating a structure of a capacitive flexible pressure sensor according to a second exemplary embodiment of the present invention.

FIGS. 6 and 7 illustrate capacitive flexible pressure sensors according to exemplary embodiments of the present invention.

The pressure sensor may use a scheme of sensing a magnitude of an applied pressure by measuring a capacitance value changed depending on the applied pressure, in addition to a scheme of sensing a magnitude of an applied pressure by measuring a resistance value changed depending on the applied pressure, as described above with reference to FIGS. 3 to 5.

Forms of capacitive flexible pressure sensors implemented using an amorphous metal according to the present invention (as an example, any one of FeZr, CoNi, La—Al_Cu, Al—Sc, ZrTiCuNiBe, AuSi, CuZr, CuPd, CuCo, CuPdCoP, PdAgSi, PdAgSiP, PdAgSiGe, PtCuAgPBSi, CuZrTi, CuZrTiNi, and CuZrTiAlBe) will be described with reference to FIGS. 6 and 7.

The pressure sensor illustrated in FIG. 6 includes a flexible substrate 100, a conductive layer 200, and a counter electrode 300, similar to the pressure sensor described above with reference to FIGS. 3 to 5. However, a position at which the conductive layer 200 is deposited is different from that of the piezo-resistive pressure sensor.

The flexible substrate 100 may have a structure in which a plurality of micro-sized structure bodies 110 are formed of a flexible material, for example, a silicon based rubber such as polydimethylsiloxane (PDMS), polyurethane, or the like, on one surface of a flexible polyethylene phthalate (PET) substrate, a polycarbonate (PC) substrate, a polyimide (PI) substrate, or a glass substrate having a thickness of several hundreds of micrometers.

Here, the plurality of micro-sized structure bodies 110 having a pyramidal shape are formed on one surface of the flexible substrate 100.

The flexible substrate having the micro-sized structure bodies 110 having the pyramid shape may be formed using a silicon mold that may mold the flexible substrate. In addition, the plurality of micro-sized structure bodies 110 may have any one of a cylindrical shape, a conical shape, and a poly-prismatic shape, in addition to the pyramidal shape.

The conductive layer 200 is deposited on an opposite surface to one surface of the flexible substrate 100 on which the plurality of micro-sized structure bodies 110 are formed, and is formed of an amorphous metal. In addition, any one of a low resistance metal, a crystalline metal, and an oxidation resistant metal may be additionally deposited as a passivation layer on a surface of the conductive layer 200 in order to increase conductivity of the conductive layer 200 and prevent oxidation of the conductive layer 200. Typically, a metal such as gold (Au) or platinum (Pt) may be additionally deposited.

The counter electrode 300 is positioned on the plurality of micro-sized structure bodies 110 on the flexible substrate 100, and is formed of an amorphous metal. Any one of a low resistance metal, a crystalline metal, and an oxidation resistant metal may be additionally deposited as a passivation layer on a surface of the counter electrode 300 in order to increase conductivity of the counter electrode 300 and prevent oxidation of the counter electrode 300. Typically, a metal such as gold (Au) or platinum (Pt) may be additionally deposited on the surface of the counter electrode 300.

In addition, a capacitance value measured between the counter electrode 300 and the conductive layer 200 is in proportion to a distance between the counter electrode 300 and the conductive layer 200. In the case in which a pressure is applied to the counter electrode 300, the plurality of micro-sized structure bodies 110 on the flexible substrate 100 are pressed, and a distance between the counter electrode 300 and the conductive layer 200 is decreased.

Therefore, in the pressure sensor illustrated in FIG. 6, the distance between the conductive layer 200 and the counter electrode 300 is changed depending on a pressure transferred from the outside, and a capacitance value between the conductive layer 200 and the counter electrode 300 changed due to the changed distance is measured to sense information on the transferred pressure.

The pressure sensor illustrated in FIG. 7 also includes a flexible substrate 100, a conductive layer 200, and a counter electrode 300. Here, since the flexible substrate 100 has been described above, a description therefor will be omitted.

The conductive layer 200 is deposited on one surface of the flexible substrate 100 on which the plurality of micro-sized structure bodies 110 are formed, and is formed of an amorphous metal.

The counter electrode 300 has a structure in which a flexible insulating substrate 320 and a metal layer 310 formed of an amorphous metal on one surface of the insulating substrate 320 are stacked. In addition, the counter electrode 300 is positioned on the conductive layer 200 so that the insulating substrate 320 faces the conductive layer 200.

Therefore, in the case in which an external pressure is applied to the pressure sensor illustrated in FIG. 7, a capacitance value changed while a distance between the metal layer 310 of the counter electrode 300 and the conductive layer 200 being decreased is measured, and information on the transferred pressure is sensed. The capacitive pressure sensor having the structure illustrated in FIG. 7 unlike the structure illustrated in FIG. 6 may also be implemented.

Hereinabove, the pressure sensors according to exemplary embodiments of the present invention have been described.

Next, a structure of a novel flexible bimodal sensor that may simultaneously sense a pressure and a temperature as an element for an electronic skin using an amorphous metal will be described with reference to FIG. 8.

Figure 8:
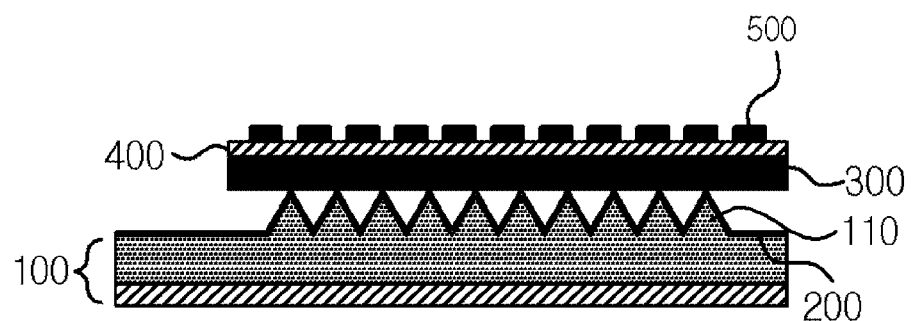
FIG. 8 is a view illustrating a structure of a flexible bimodal sensor capable of simultaneously sensing a pressure and a temperature according to a first exemplary embodiment of the present invention.

As illustrated in FIG. 8, a novel flexible bimodal sensor according to an exemplary embodiment of the present invention includes a conductive layer formed of an amorphous metal (for example, any one of FeZr, CoNi, La—Al_Cu, Al—Sc, ZrTiCuNiBe, AuSi, CuZr, CuPd, CuCo, CuPdCoP, PdAgSi, PdAgSiP, PdAgSiGe, PtCuAgPBSi, CuZrTi, CuZrTiNi, and CuZrTiAlBe) on a flexible substrate and further includes a component for sensing a temperature to simultaneously sense the pressure and the temperature. In detail, FIG. 8 illustrates the flexible bimodal sensor according to an exemplary embodiment further including the component for sensing a temperature, in addition to the components of the piezo-resistive pressure sensor illustrated in FIG. 3.

Referring to FIG. 8, the novel flexible bimodal sensor according to an exemplary embodiment of the present invention includes a flexible substrate 100, a conductive layer 200, a counter electrode 300, a flexible insulating substrate 400, and a conducting wire 500.

The flexible substrate 100 may have a structure in which a plurality of micro-sized structure bodies 110 are formed of a flexible material, for example, a silicon based rubber such as polydimethylsiloxane (PDMS), polyurethane, or the like, on one surface of a flexible polyethylene phthalate (PET) substrate, a polycarbonate (PC) substrate, a polyimide (PI) substrate, or a glass substrate having a thickness of several hundreds of micrometers.

Here, the plurality of micro-sized structure bodies 110 having a pyramidal shape are formed on one surface of the flexible substrate.

The plurality of micro-sized structure bodies 110 may have any one of a cylindrical shape, a conical shape, and a poly-prismatic shape, in addition to the pyramidal shape.

The conductive layer 200 is deposited on one surface of the flexible substrate on which the plurality of micro-sized structure bodies 110 are formed, and is formed of an amorphous metal. Therefore, the conductive layer 200 is deposited on the plurality of micro-sized structure bodies 110. In addition, any one of a low resistance metal, a crystalline metal, and an oxidation resistant metal may be additionally deposited as a passivation layer on the conductive layer 200 in order to increase conductivity of the conductive layer 200 and prevent oxidation of the conductive layer 200. Typically, a metal such as gold (Au) or platinum (Pt) may be additionally deposited.

The counter electrode 300 is positioned on the conductive layer 200 and receives a pressure transferred from the outside. It is preferable that the counter electrode 300 is also formed of an amorphous metal, similar to the conductive layer 200. In addition, any one of a low resistance metal, a crystalline metal, and an oxidation resistant metal may be additionally deposited as a passivation layer on a surface of the counter electrode 300 in order to increase conductivity of the counter electrode 300 and prevent oxidation of the counter electrode 300. Typically, a metal such as gold (Au) or platinum (Pt) may be additionally deposited.

The micro-sized structure bodies 110 having the pyramidal shape are pressed depending on a pressure transferred to the counter electrode 300, such that a contact area between the counter electrode 300 and the conductive layer 200 is changed.

Figure 9:
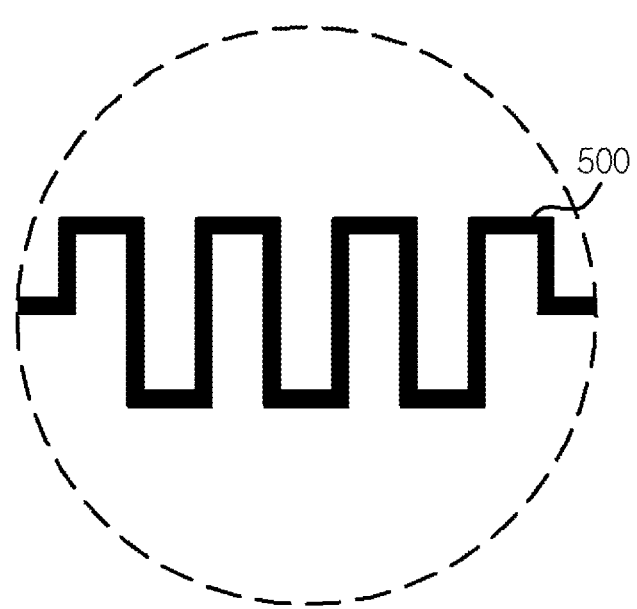
FIG. 9 is a plan view of a conducting wire illustrated in FIG. 8.

The flexible insulating substrate 400 is positioned on an upper surface of the counter electrode 300. In addition, the conducting wire 500 is formed of an amorphous metal, and is repeatedly arranged in a zigzag pattern at a predetermined interval on an upper surface of the insulating substrate 400, as illustrated in FIG. 9. The reason why the conducting wire 500 is arranged in the zigzag pattern is to have a predetermined level of resistance value even at room temperature in order to more accurately sense a temperature. A metal such as gold (Au) or platinum (Pt) may be additionally deposited as a passivation layer on a surface of the conducting wire 500 in order to prevent oxidation of the conducting wire 500.

The flexible insulating substrate 400 blocks electrical connection between the conducting wire 500 and the counter electrode 300. In addition, the conducting wire 500 on the insulating substrate 400 is arranged in the zigzag pattern to have a predetermined resistance value, and represents a resistance value changed depending on a temperature change transferred from the outside.

Therefore, the bimodal sensor according to an exemplary embodiment of the present invention may measure a resistance value of the conducting wire 500 changed depending on a temperature transferred to the conducting wire 500 to sense information on the transferred temperature, when external physical energy is applied onto the flexible insulating substrate 400 and the conducting wire 500. In addition, the bimodal sensor may measure a resistance value changed while a contact area between the counter electrode 300 and the conductive layer 200 being changed depending on a pressure applied thereto, thereby making it possible to sense information on the applied pressure.

In the bimodal sensor according to an exemplary embodiment of the present invention, the conducting wire 500 for sensing a temperature is also formed of an amorphous metal, thereby making it possible to implement a stretchable element for an electronic skin.

Hereinabove, the flexible bimodal sensor according to an exemplary embodiment including additional components 400 and 500 for sensing a temperature in addition to the components of the piezo-resistive pressure sensor has been described with reference to FIG. 8.

In addition, the additional components (the flexible insulating substrate 400 and the conducting wire 500) for sensing a temperature described above are provided on the upper surface of the counter electrode 300 of the capacitive pressure sensor illustrated in FIGS. 6 and 7, thereby making it possible to implement the flexible bimodal sensor according to the present invention.

In addition, in the case of the piezo-resistive pressure sensor illustrated in FIG. 5, the flexible insulating substrate 320 is included in the counter electrode 300, and thus, only the conducting wire 500 is additionally disposed on the flexible insulating substrate 320 of the counter electrode 300 positioned on a surface of the sensor without adding a separate insulating substrate, thereby making it possible to implement the flexible bimodal sensor according to the present invention.

The piezo-resistive or capacitive pressure sensor according to an exemplary embodiment of the present invention described above includes the conductive layer formed of the amorphous metal to have stretchable characteristics that a predetermined level of conductivity may be maintained even in a state in which physical external force (bending, elongation, or the like) is present, as compared with an existing conductive layer formed of a carbon nano material. In addition, the conductive layer formed of the amorphous metal is excellently attached onto the flexible substrate and the plurality of micro-sized structure bodies provided on the flexible substrate.

In addition, since the conductive layer formed of the amorphous metal has a relatively low resistance value, it may lower an operation voltage of the pressure sensor to $\frac{1}{50}$, as compared with an existing conductive layer formed of a carbon nano element or a composite of an organic material and an elastic material. In other words, the pressure sensor having the existing conductive layer formed of the composite of the organic material and the elastic material might measure a change in a resistance value depending on a pressure applied from the outside thereto when an operation voltage of about 5 to 10V is applied thereto. However, the pressure sensor having the conductive layer formed of the amorphous metal according to the present invention may measure a change in a resistance value depending on a pressure applied from the outside thereto even though an operation voltage of about 0.1V is applied thereto.

Therefore, the operation voltage of the pressure sensor may be significantly lowered as compared with that of an existing pressure sensor. Further, cells are formed at a small size so as to implement the electronic skin, and an electrical signal is easily sensed with respect to an external physical stimulus without noise even at a small cell area.

In addition, the flexible bimodal sensor according to an exemplary embodiment of the present invention is a novel element for an electronic skin that may simultaneously sense a pressure and a temperature while having the advantages of the pressure sensor described above.

The present invention should not be construed to being limited to the above-mentioned exemplary embodiment. The present invention may be applied to various fields and may be variously modified by those skilled in the art without departing from the scope of the present invention claimed in the claims. Therefore, it is obvious to those skilled in the art that these alterations and modifications fall within the scope of the present invention.

What is claimed is:

1. A flexible pressure sensor comprising:
   a flexible substrate having a plurality of micro-sized structure bodies formed of a flexible material on one surface thereof;
   a conductive layer deposited on one surface of the flexible substrate on which the plurality of micro-sized structure bodies are formed and consisting of an amorphous metal; and
   a counter electrode positioned on the conductive layer,
   wherein the flexible pressure sensor is configured to measure a resistance value generated by a change in a contact area between the counter electrode and the conductive layer depending on a pressure transferred from the outside through the conductive layer and the counter electrode to sense information on the transferred pressure, and
   wherein the counter electrode is entirely formed of the amorphous metal, or has a structure in which a flexible insulating substrate and a metal layer formed of an amorphous metal on one surface of the flexible insulating substrate are stacked, and the metal layer is positioned on the conductive layer so as to face the conductive layer.

2. The flexible pressure sensor of claim 1, wherein the plurality of micro-sized structure bodies have any one of a pyramidal shape, a cylindrical shape, a conical shape, and a poly-prismatic shape.

3. The flexible pressure sensor of claim 1, wherein the amorphous metal is any one of FeZr, CoNi, La—Al_Cu, Al—Sc, ZrTiCuNiBe, AuSi, CuZr, CuPd, CuCo, CuPdCoP, PdAgSi, PdAgSiP, PdAgSiGe, PtCuAgPBSi, CuZrTi, CuZrTiNi, and CuZrTiAlBe.

4. The flexible pressure sensor of claim 1, wherein a passivation layer formed of any one of a low resistance metal, a crystalline metal, and an oxidation resistant metal is additionally deposited on the conductive layer in order to increase conductivity of the conductive layer and prevent oxidation of the conductive layer.

5. A flexible bimodal sensor comprising:
a flexible substrate having a plurality of micro-sized structure bodies formed of a flexible material on one surface thereof;
a conductive layer deposited on one surface of the flexible substrate on which the plurality of micro-sized structure bodies are formed and formed of an amorphous metal;
a counter electrode positioned on the conductive layer and formed of an amorphous metal;
a flexible insulating substrate positioned on an upper surface of the counter electrode; and
a conducting wire repeatedly arranged in a zigzag pattern at a predetermined interval on an upper surface of the flexible insulating substrate and formed of an amorphous metal,
wherein the flexible bimodal sensor measures a resistance value between the counter electrode and the conductive layer changed by a change in a contact area between the counter electrode and the conductive layer depending on a pressure transferred from the outside to sense information on the transferred pressure, and
measures a resistance value of the conducting wire changed depending on a temperature transferred from the outside to sense information on the transferred temperature.

6. The flexible bimodal sensor of claim 5, wherein the amorphous metal is any one of FeZr, CoNi, La—Al_Cu, Al—Sc, ZrTiCuNiBe, AuSi, CuZr, CuPd, CuCo, CuPdCoP, PdAgSi, PdAgSiP, PdAgSiGe, PtCuAgPBSi, CuZrTi, CuZrTiNi, and CuZrTiAlBe.

7. The flexible bimodal sensor of claim 5, wherein a passivation layer formed of any one of a low resistance metal, a crystalline metal, and an oxidation resistant metal is additionally deposited on surfaces of the conductive layer, the counter electrode, and the conducting wire formed of the amorphous metals in order to increase conductivity of the conductive layer, the counter electrode, and the conducting wire and prevent oxidation of the conductive layer, the counter electrode, and the conducting wire.

8. A flexible pressure sensor comprising:
a flexible substrate having a plurality of micro-sized structure bodies formed of a flexible material on one surface thereof;
a conductive layer deposited on one surface of the flexible substrate on which the plurality of micro-sized structure bodies are formed and formed of an amorphous metal; and
a counter electrode positioned on the conductive layer;
a substrate positioned on an upper surface of the counter electrode; and
a conducting wire repeatedly arranged in a zigzag pattern at a predetermined interval on an upper surface of the substrate and formed of an amorphous metal,
wherein the flexible pressure sensor is configured to measure a resistance value generated by a change in a contact area between the counter electrode and the conductive layer depending on a pressure transferred from the outside through the conductive layer and the counter electrode to sense information on the transferred pressure.

9. The flexible pressure sensor of claim 8, wherein the flexible pressure sensor further measures a resistance value of the conducting wire changed depending on a temperature transferred from the outside to sense information on the transferred temperature.

* * * * *